United States Patent
Crow et al.

(10) Patent No.: US 12,233,326 B2
(45) Date of Patent: Feb. 25, 2025

(54) ELECTRONIC ATHLETIC TRAINING SYSTEM

(71) Applicant: Dick's Sporting Goods, Inc., Coraopolis, PA (US)

(72) Inventors: Tyler Crow, Bethel Park, PA (US); Charles P. Larson, Coraopolis, PA (US)

(73) Assignee: DICK'S SPORTING GOODS, INC., Coraopolis, PA (US)

(*) Notice: Subject to any disclaimer, the term of this patent is extended or adjusted under 35 U.S.C. 154(b) by 476 days.

(21) Appl. No.: 17/124,860

(22) Filed: Dec. 17, 2020

(65) Prior Publication Data

US 2021/0187354 A1 Jun. 24, 2021

Related U.S. Application Data

(60) Provisional application No. 62/949,815, filed on Dec. 18, 2019.

(51) Int. Cl.
| | |
|---|---|
| A63B 71/06 | (2006.01) |
| A63B 24/00 | (2006.01) |
| A63B 71/02 | (2006.01) |
| G08B 5/36 | (2006.01) |

(52) U.S. Cl.
CPC .......... *A63B 71/03* (2020.08); *A63B 24/0062* (2013.01); *A63B 24/0075* (2013.01); *A63B 71/0622* (2013.01); *A63B 2220/805* (2013.01); *A63B 2225/50* (2013.01); *A63B 2243/0037* (2013.01); *G08B 5/36* (2013.01)

(58) Field of Classification Search
None
See application file for complete search history.

(56) References Cited

U.S. PATENT DOCUMENTS

| | | | |
|---|---|---|---|
| 5,485,700 A | 1/1996 | Van Vranken | |
| 5,669,833 A | 9/1997 | Stone | |
| 7,309,234 B2 | 12/2007 | Mathog | |
| 7,798,920 B1 | 9/2010 | Cortes | |
| 7,951,045 B1 * | 5/2011 | Brader | A63B 71/06 |
| | | | 482/3 |
| 8,602,584 B2 * | 12/2013 | Ghafoori | H05B 47/155 |
| | | | 362/186 |
| 9,266,002 B2 | 2/2016 | Dunser | |
| 9,511,260 B2 | 12/2016 | Molyneux et al. | |
| 9,566,489 B2 | 2/2017 | De Graaf et al. | |
| 10,279,216 B2 | 5/2019 | D'Andrade et al. | |

(Continued)

FOREIGN PATENT DOCUMENTS

| | | | |
|---|---|---|---|
| CN | 209752120 | * | 12/2019 |
| CN | 209752120 U | * | 12/2019 |

(Continued)

*Primary Examiner* — Shila Jalalzadeh Abyaneh
(74) *Attorney, Agent, or Firm* — Foley & Lardner LLP

(57) ABSTRACT

An electronic athletic training system includes a first detection device and a second detection device, each of which includes a transmitter, a receiver, one or more visual indicators, a processor, and a computer-readable storage medium. A transmitter of one detection device emits a light beam to the receiver of the other detection device when the transmitter is in proximity to the receiver. A detection device performs one or more actions in response to detecting that the light beam has been broken.

20 Claims, 9 Drawing Sheets

(56) References Cited

U.S. PATENT DOCUMENTS

| | | | |
|---|---|---|---|
| 2011/0148039 A1* | 6/2011 | Klinnert | A63B 24/0084 |
| | | | 273/148 R |
| 2012/0064495 A1* | 3/2012 | Tybon | G01S 19/51 |
| | | | 434/247 |
| 2015/0065273 A1 | 3/2015 | Lake | |
| 2015/0116122 A1 | 4/2015 | Laws et al. | |
| 2016/0030825 A1 | 2/2016 | Mazzanobile et al. | |
| 2016/0038820 A1 | 2/2016 | Junaid et al. | |
| 2016/0199715 A1 | 7/2016 | Fuccillo et al. | |
| 2016/0271447 A1 | 9/2016 | Cucco | |
| 2017/0361190 A1* | 12/2017 | Del Monte | A63B 71/03 |
| 2019/0232138 A1* | 8/2019 | Bartels | A63B 69/0053 |

FOREIGN PATENT DOCUMENTS

| | | | | |
|---|---|---|---|---|
| WO | WO-2017041141 A1 * | 3/2017 | | H05B 37/02 |
| WO | WO-2018202940 A1 * | 11/2018 | | A63B 63/004 |
| WO | WO-2018215812 A1 * | 11/2018 | | |

* cited by examiner

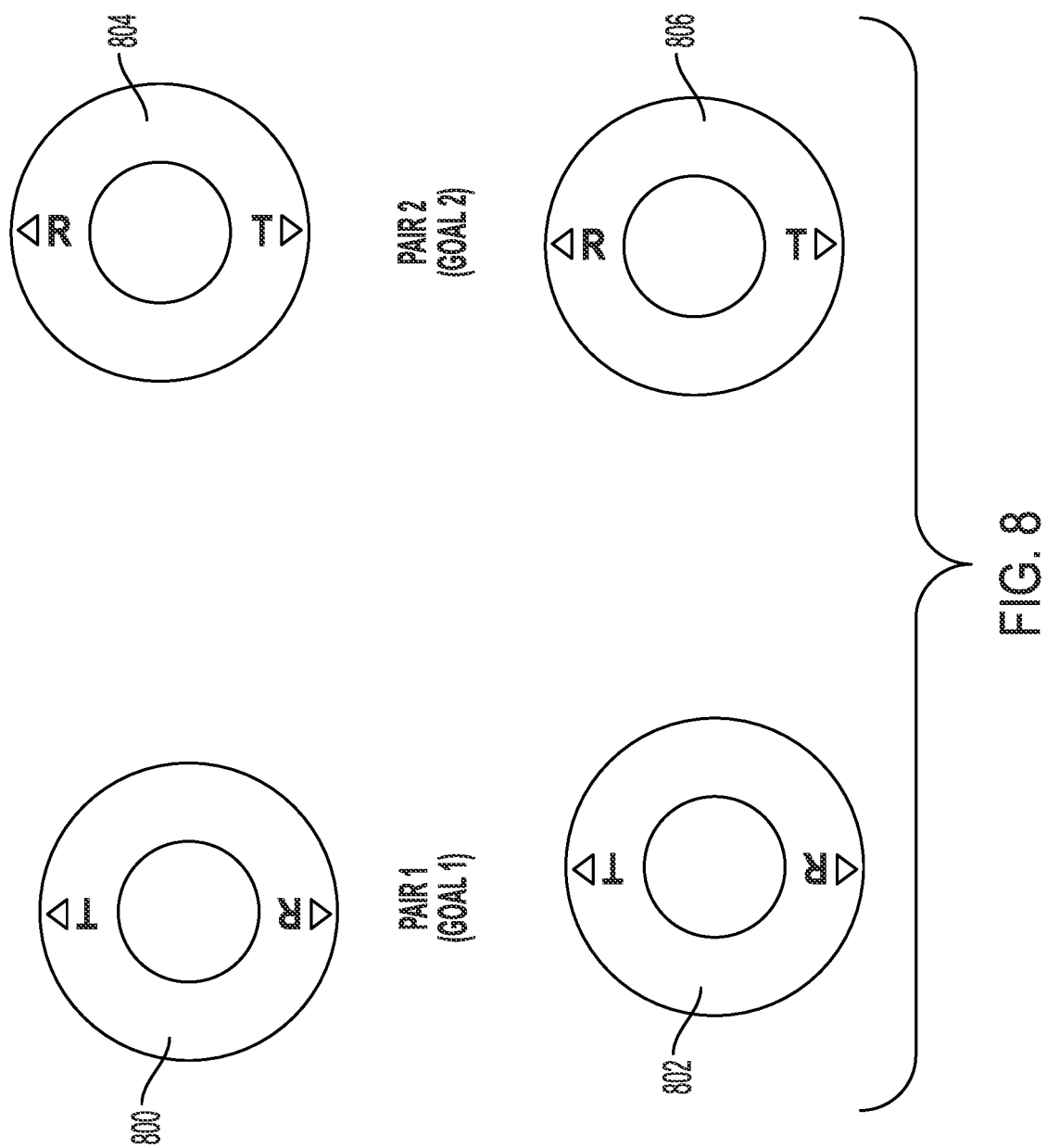

ELECTRONIC ATHLETIC TRAINING SYSTEM

RELATED APPLICATIONS AND CLAIM OF PRIORITY

This patent document claims priority to U.S. provisional patent application No. 62/949,815, filed Dec. 18, 2019, the disclosure of which is fully incorporated into this document by reference.

BACKGROUND

Cones are typically used to help athletes perform training exercises. For example, cones may be set up in a particular configuration to define a particular course through which a game piece (e.g., a ball, a puck, etc.) or a player is to proceed to complete a certain drill or exercise. As another example, cones may be arranged to indicate an area into which a game piece should be aimed. For instance, for soccer drills, two cones may be arranged in proximity to one another to define a goal between the cones through which a soccer ball is to be aimed during a shot.

These training exercises or drills can be used to train various athletic skills such as, for example, control, speed, agility, coordination and/or the like. However, typical cones do not provide feedback to a player or coach regarding the completion of an exercise, drill or portion of exercise or drill. In addition, the use of typical cones can leave the order in which a drill is to be completed up to the interpretation of the player.

SUMMARY

In various embodiments, an electronic athletic training system includes a first detection device and a second detection device. The first detection device includes a first transmitter located on a first side of the first detection device, a first receiver located on a second side of the first detection device that is opposite the first side, one or more first visual indicators, a first processor in communication with the first transmitter, the first receiver, and the one or more first visual indicators, and a first computer-readable storage medium. The second detection device includes a second transmitter located on a first side of the second detection device, a second receiver located on a second side of the second detection device that is opposite the first side of the second detection device, one or more second visual indicators, a second processor in communication with the second transmitter, the second receiver, and the one or more second visual indicators, and a second computer-readable storage medium. The first computer-readable storage medium includes one or more programming instructions that, when executed, cause the first processor to cause the first transmitter to emit a light beam to the second receiver when the first transmitter is in proximity to the second receiver. The second computer-readable storage medium includes one or more programming instructions that, when executed, cause the second processor to detect when the light beam is broken and perform one or more actions in response to detecting that the light beam has been broken.

The first detection device may include a selection mechanism having a plurality of positions such that each position corresponds to one of a plurality of settings of the first detection device. The setting may include one or more of an off setting, a random pairs setting, a dribble lights on setting, a dribble lights off setting, or a goal setting.

The second detection device may include a selection mechanism having a plurality of positions such that each position corresponds to a setting of the second detection device. The setting may include one or more of an off setting, a random pairs setting, a dribble lights on setting, a dribble lights off setting, or a goal setting.

The second detection device may perform one or more actions in response to detecting that the light beam has been broken by sending a message to the first detection device that includes one or more instructions that instruct the first processor to cause one or more of the one or more first visual indicators to illuminate, or cause one or more of the one or more first visual indicators to turn off.

The second detection device may perform one or more actions in response to detecting that the light beam has been broken by causing one or more of the one or more second visual indicators to illuminate, or causing one or more of the second visual indicators to turn off.

The second detection device may perform one or more actions in response to detecting that the light beam has been broken by sending a message to the first detection device that includes one or more instructions that instruct the first processor to cause one or more of the one or more first visual indicators to turn off, and cause the first transmitter to continue to emit the light beam to the second receiver after the light beam has been broken.

The second detection device may perform one or more actions in response to detecting that the light beam has been broken by causing one or more of the one or more second visual indicators to turn off, and sending a message to the first detection device that includes one or more instructions that instruct the first processor to cause the first transmitter to continue to emit the light beam to the second receiver after the light beam has been broken.

In various embodiments, a method of performing a training exercise using an electronic athletic system includes detecting, by a first detection device, that a selection mechanism of the first detection device has been placed in a position that corresponds to a setting. The first detection device includes a first transmitter and a first receiver. The method includes detecting, by a second detection device, that a selection mechanism of the second detection device has been placed in a position that corresponds to the setting. The second detection device includes a second transmitter and a second receiver. The first detection device and the second detection device form a first pair. The method includes emitting, by the first transmitter, a light beam and receiving, by the second receiver, the light beam when the first transmitter is aligned with the second receiver. The method includes detecting, by a third detection device, that a selection mechanism of the third detection device has been placed in a position that corresponds to the setting. The third detection device includes a third transmitter and a third receiver. The method includes detecting, by a fourth detection device, that a selection mechanism of the fourth detection device has been placed in a position that corresponds to the setting. The fourth detection device includes a fourth transmitter and a fourth receiver. The third detection device and the fourth detection device form a second pair. The method includes emitting, by the third transmitter, a second light beam, causing one or more visual indicators of the third detection device and/or one or more visual indicators of the fourth detection device to be illuminated, and receiving, by the fourth receiver, the second light beam, when the third transmitter is aligned with the fourth receiver.

The method may include detecting, by the fourth detection device, that the second light beam has been broken, sending a message to the third detection device instructing the third detection device to turn off its one or more visual indicators, and sending a second message to the first detection device and/or the second detection device. The second message may include an indication that the second light beam has been broken.

The method may include receiving, by the first detection device and/or the second detection device, the second message, and in response to receiving the second message identifying one of the first pair or the second pair, and in response to identifying the first pair, causing one or more visual indicators of the first detection device and one or more visual indicators of the second detection device to illuminate.

The method may include receiving, by the first detection device and/or the second detection device, the second message. In response to receiving the second message, the method may include identifying one of the first pair or the second pair, and in response to identifying the second pair, sending one or more instructions to the third detection device to illuminate its one or more visual indicators, and sending one or more instructions to the fourth detection device to illuminate its one or more visual indicators.

BRIEF DESCRIPTION OF THE DRAWINGS

FIG. 8 illustrates an example configuration of detection devices operating in a "goal" setting.

DETAILED DESCRIPTION

Figure 1:
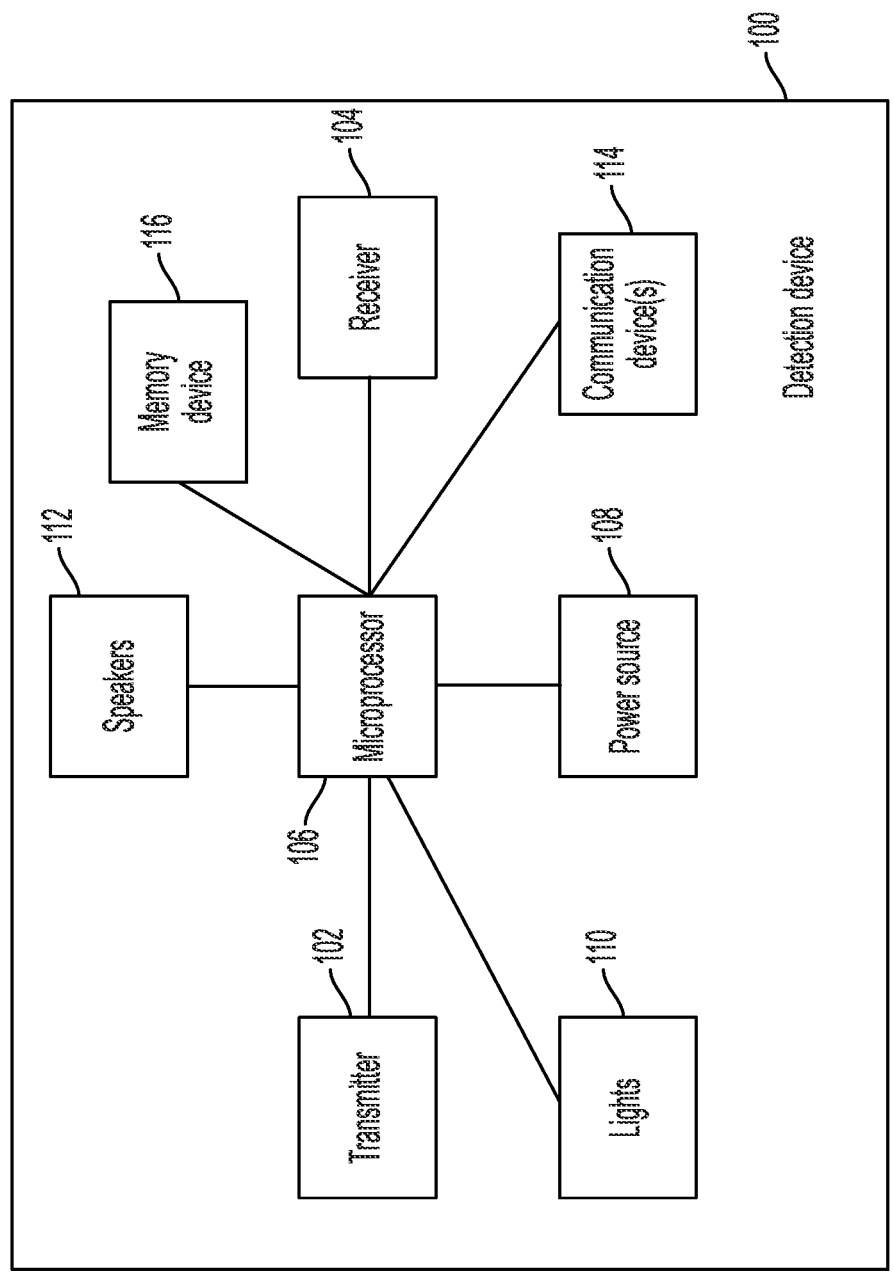
FIG. 1 illustrates example components of a detection device.

FIG. 1 illustrates example components of a detection device according to an embodiment. As illustrated by FIG. 1, a detection device 100 may include one or more transmitters 102, one or more receivers 104, a processor 106, a power source 108 and/or one or more visual indicators 110. A transmitter 102 may be an optical transmitter, such as, for example an infrared transmitter. A receiver 104 may be an optical receiver such as, for example, an infrared receiver. The power source 108 may include one or more batteries. Optionally, one or more detection devices may include one or more speakers 112.

In various embodiments, a transmitter 102 may be located opposite a receiver 104 of a detection device. For example, a transmitter may be located on a left side of a detection device and a receiver may be located on an opposite side of the detection device. This may allow multiple detection devices to be used together, as discussed in more detail below.

The processor 106 is a central processing device, configured to perform calculations and logic operations required to execute programming instructions. An example of a processor may be a microprocessor and/or the like. As used in this document and in the claims, the terms "processor" may refer to a single processor or any number of processors in a set of processors that collectively perform a set of operations.

A detection device may include one or more data stores or other memory devices 114. Read only memory (ROM), random access memory (RAM), flash memory, hard drives and other devices capable of storing electronic data constitute examples of data stores or memory devices. A data store or memory device may include a single device or a collection of devices across which data and/or instructions are stored. Various embodiments of the invention may include a computer-readable medium containing programming instructions that are configured to cause one or more processors to perform the functions described in this disclosure.

The processor 106 may be in communication with one or more transmitters 102, one or more receivers 104 and/or one or visual indicators 110. For example, a receiver 104 may provide a processor 106 with information that it receives, and the processor may use this information to perform one or more actions at the detection device such as, for example, causing one or more visual indicators 110 to be illuminated. In various embodiments, one or more visual indicators 110 may be light-emitting diodes (LEDs), light panels, light arrays, and/or the like.

In various embodiments, detection devices 100 may communicate with one or more electronic devices via one or more communication devices 114. One or more communication devices 114 may facilitate communication between a detection device and one or more other detection devices and/or other electronic devices via one or more wireless communication protocols. Examples of communication devices 114 may include, for example, a wireless communication transmitter, receiver, transceiver, and/or the like.

For instance, detection devices 100 may communicate with one another via short range wireless communication such as, for example, near field communication (NFC), radio frequency identification, Bluetooth, Wi-Fi, Zigbee, and/or the like.

A detection device 100 may include a short range communication receiver, transmitter such as, for example, a Bluetooth antenna, an NFC chip, an RFID tag, a Zigbee chip, a wireless transmitter, receiver and/or transceiver, and/or the like. A detection device 100 may communicate with one another via radio frequency (RF) communication. A detection device 100 may include an RF transmitter, an RF receiver and/or an RF transceiver.

Figure 2A:
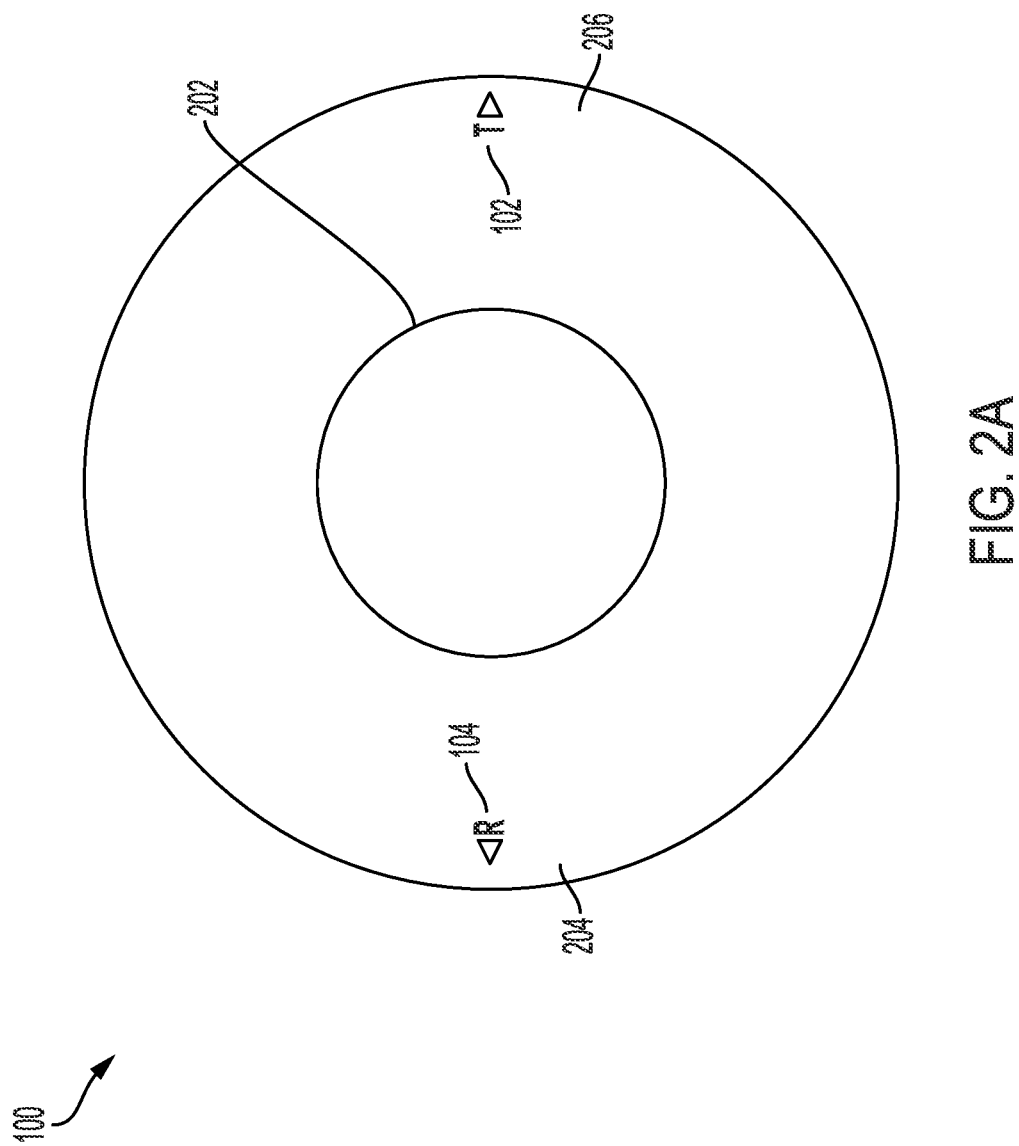
FIG. 2A illustrates an external view of an example detection device.

FIG. 2A illustrates an external view of an example detection device 100 according to an embodiment. The detection device 100 illustrated in FIG. 2A has a generally circular shape with an opening 202 through its center. A detection device 100 having this configuration may receive at least a portion of a training cone through its opening 202. In this embodiment, the detection device 100 may be positioned on a training cone so that it is elevated from the ground.

Although this disclosure illustrates a generally circular detection device 100 with an opening 202 through its center, it is understood that detection devices having different shapes or configurations may be used within the scope of this disclosure. For example, a detection device may be generally circular without an opening through its center. As another example, a detection device may be square, rectangular, oblong, triangular and/or any other suitable shape, and may or may not have an opening through at least a portion of the device.

As illustrated by FIG. 2A, a receiver 104 may be located near a first side 204 of the detection device 100, and a transmitter 102 may be located on a side 206 of the detection device that is opposite the side near which the receiver is located. The position of the transmitter 102 and/or receiver 104 may be indicated by one or more visual designations. A visual designation may be a character, word, symbol, image and/or the like. For example, as illustrated in FIG. 2A, the position of the receiver is indicated with 'R' and the position of the transmitter is indicated with 'T'. Other visual designations may be used within the scope of this disclosure. FIG. 2A shows these visual indications on a top surface of the detection device in proximity to the component to which it corresponds. However, the placement of the visual designations may vary within the scope of this disclosure.

Figure 2B:
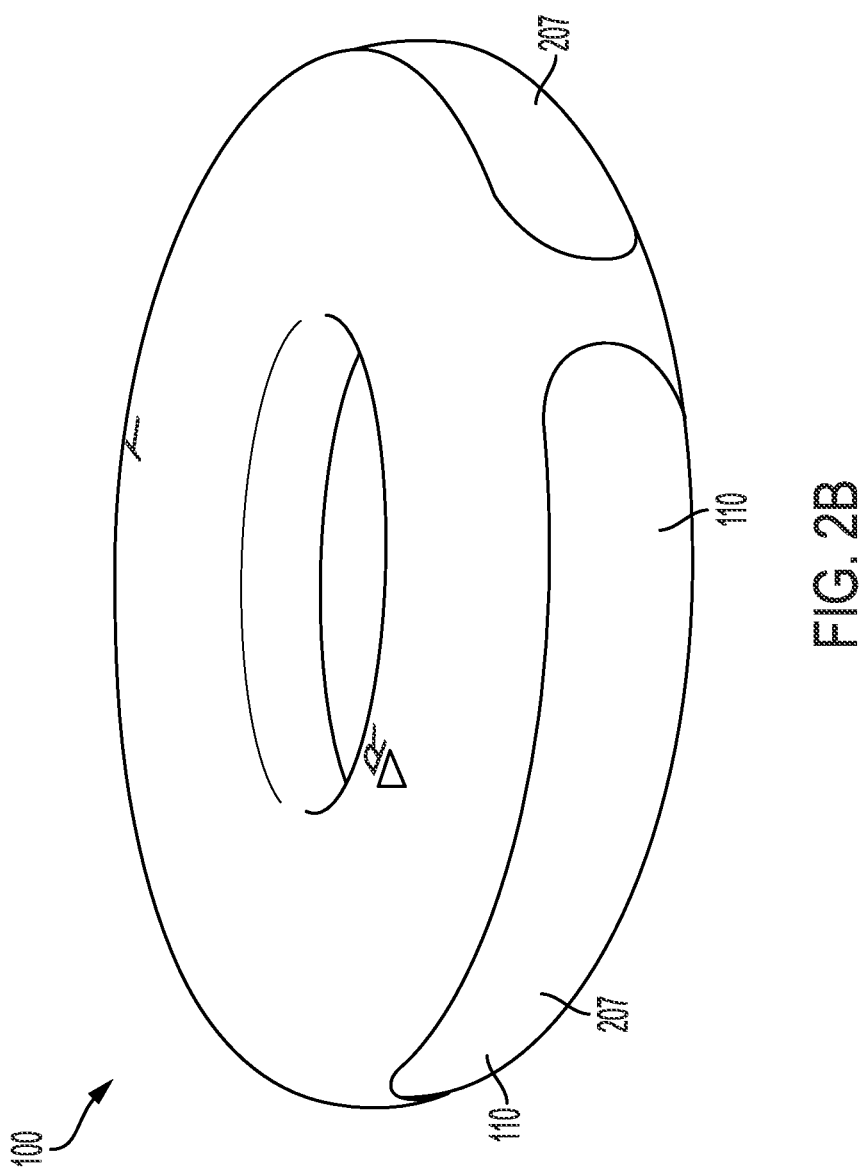
FIG. 2B illustrates an example arrangement of visual indicators of a detection device.

In various embodiments, the visual indicators 110 may be positioned at various locations of the detection device so that they are visible to a player. FIG. 2B illustrates an example arrangement of visual indicators according to an embodiment. As shown in FIG. 2B, the detection device 100 may include one or more visual indicator portions 207 which each may be associated with one or more visual indicators 110. For instance, the detection device 100 shown in FIG. 2B has four visual indicators portions 207 (two not shown), and each visual indicators portion corresponds to two lights 110. Additional and/or alternate visual indicator portions or visual indicators may be used within the scope of this disclosure.

A visual indicator portion 207 may be fabricated from a transparent, translucent or semi-transparent or semi-translucent material. In this way, when a corresponding visual indicator 110 is illuminated, it may emit light through a visual indicator portion 207. In various embodiments, one or more of the visual indicator portions may have a color so that the light that is emitted through the visual indicator portion appears to have a color as well. In various embodiments, the visual indicator may be illuminated all together or one at a time. In other embodiments, the visual indicator may be illuminated in a pattern, such as, for example, in a particular sequence or order. The manner in which the visual indicator are illuminated may depend on, for example, the setting of the detection device or the event that is detected, as is described in more detail below.

Figure 3:
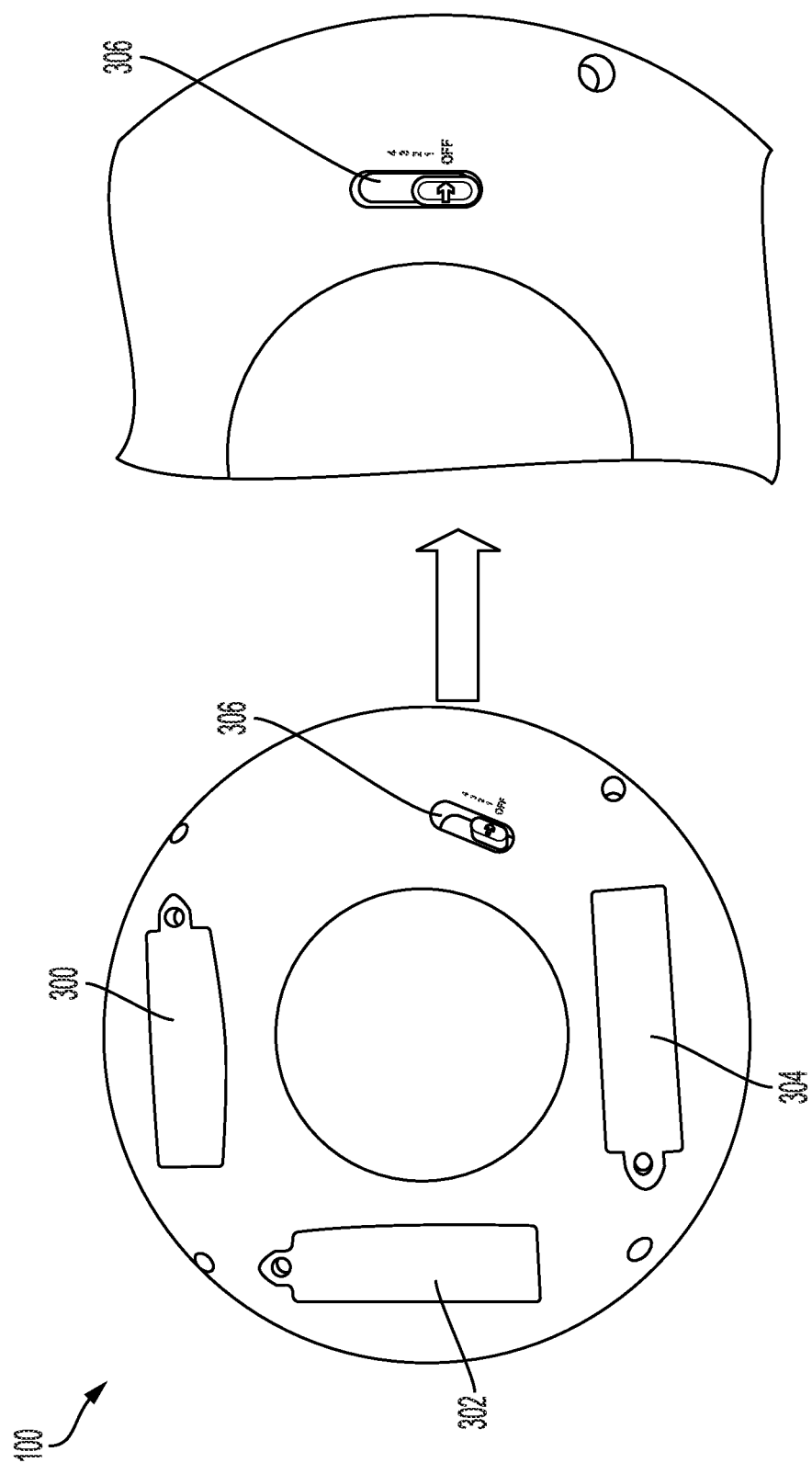
FIG. 3 illustrates a view of a bottom of an example detection device.

FIG. 3 illustrates a view of a bottom of an example detection device according to an embodiment. As illustrated by FIG. 3, the bottom may include one or more compartments 300, 302, 304 for one or more batteries. The detection device 100 illustrated in FIG. 3 includes three battery compartments 300, 302, 304, but it is understood that fewer or additional batteries may be used within the scope of this disclosure. In addition, the placement of one or more battery compartments may vary within the scope of this disclosure.

As shown in FIG. 3, a detection device 100 may include a selection mechanism 306. A selection mechanism refers to a mechanism that may be moved or switched between two or more positions. Each position of the selection mechanism may correspond to a mode of operation of a detection device. An example selection mechanism may be a slider switch, a toggle, a dial, a knob, one or more buttons, and/or the like. When a selection mechanism is set to a position that corresponds to a particular setting, the detection device 100 may operate in accordance with the setting. One or more settings may allow an athlete to complete different drills or exercises to improve his or her skills and/or fitness.

Figure 4:
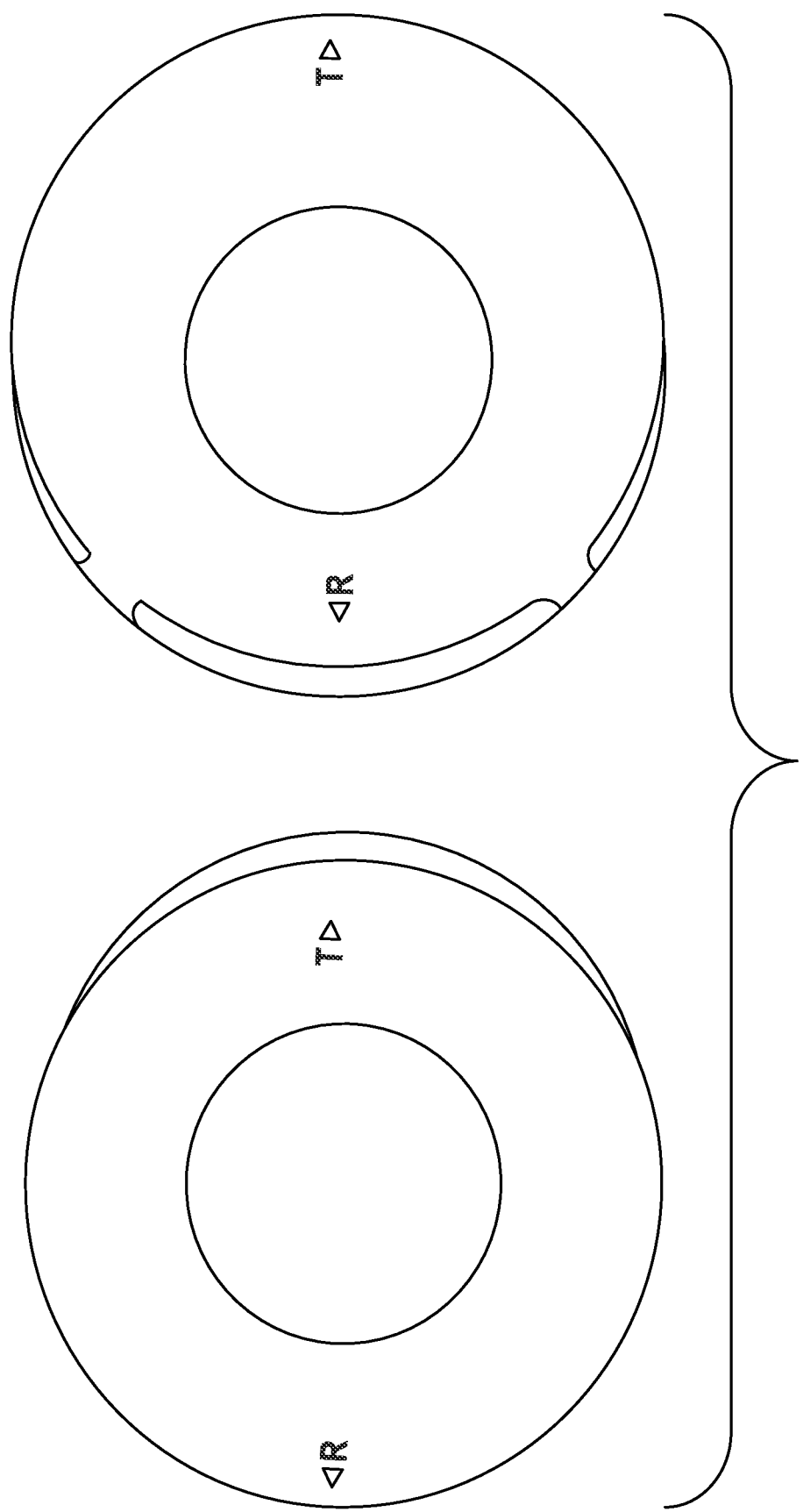
FIG. 4 illustrates an example pair of detection devices in alignment.

In various embodiments, two or more detection devices may be arranged in a particular configuration to execute a particular drill or exercise. To do so, a transmitter of one detection device may be aligned with a receiver of a different detection device. Alignment may involve placing the detection devices so that the transmitter of a first detection device is positioned within a threshold distance from a receiver of a second detection device. In various embodiments this threshold distance may be six feet. However, different threshold distances may be used within the scope of this disclosure. FIG. 4 illustrates a pair of detection devices in alignment according to an embodiment.

Because a detection device may include both a transmitter and a receiver, any number of detection devices may be arranged such that a transmitter of one detection device aligns with a receiver of another detection device. For example, multiple detection devices may be arranged in a line.

When alignment between two detection devices is achieved, one or more of the detection devices may provide a user with an indication of alignment. The indication may be a visual indication such as, for example, the illumination of one or more visual indicators. For instance, the detection device whose receiver is in alignment with another detection device may cause a visual indicator to be illuminated to indicate that alignment has been achieved. The visual indicator may be located in proximity to the receiver, and may illuminate in a specific color, such as, for example, blue.

When alignment between two detection devices is achieved, the transmitter of one detection device may emit a light beam across the gap between the two detection devices which may be received by the receiver of the other detection device. As such, the transmitter and receiver may form a light gate between the two detection devices. The light beam may be invisible to the human eye. In other embodiments, the light beam may have a color.

One or both of the detection devices of a pair may detect when the light beam is broken. The light beam may be broken in response to a game piece, such as, for example, a ball, a puck and/or the like crossing the light beam. For instance, if a player kicks a ball in the gap between a pair of detection devices, the ball will break the light beam.

As another example, a light beam may be broken in response to an athlete or other person crossing between the detection devices. For example, as part of footwork drills, an athlete may run between a pair of detection devices which may break the light beam.

When a light beam is broken, various different actions may be taken depending on the setting on which the detection devices are operating. Example settings that a detection device may operate in include, without limitation, an "off" setting, a "random pairs" setting, a "dribble weave (lights on)" setting, a "goal" setting, a "dribble weave (lights off)" setting and/or the like. In an "off" setting, a detection device may operate in a powered off or powered down mode.

Figure 5:
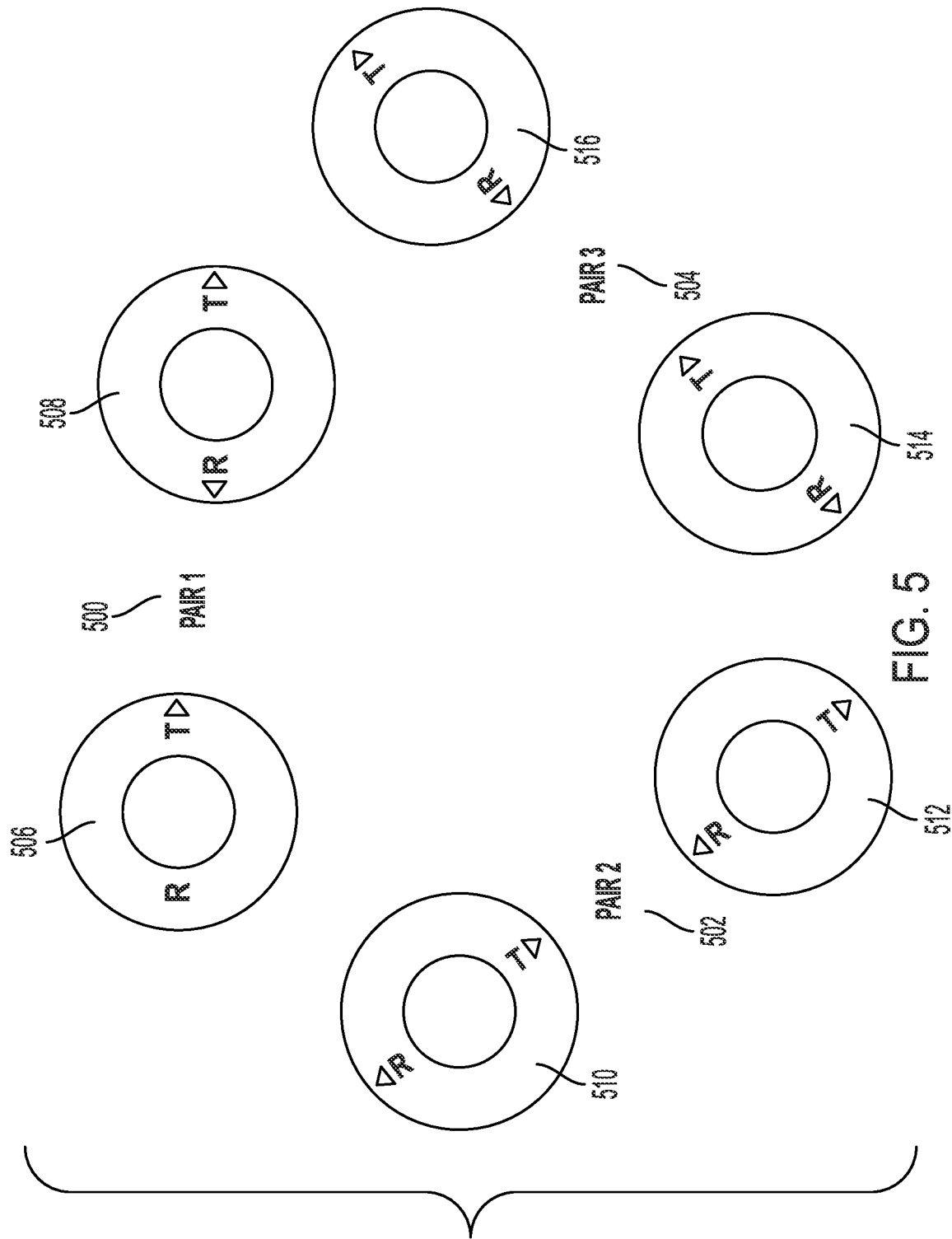
FIG. 5 illustrates three pairs of detection devices all operating in a "random pairs" setting.

The "random pairs" setting may be used for one or more pairs of detection devices. FIG. 5 illustrates three pairs of detection devices all operating in a "random pairs" setting according to an embodiment. When the detection devices are placed into "random pairs" setting (e.g., by placing the selection mechanism in a position that corresponds to the "random pairs" setting), one or more of the visual indicator of one of the three pairs may illuminate. For example, referring to FIG. 5, lights of detection devices of Pair 1 may illuminate. This illumination may indicate to an athlete that the athlete is to perform an action using the pair such as, for example, kicking a game piece between the detection devices, running through the detection devices and/or the like.

When the light beam is broken between a pair of illuminated detection devices, the visual indicators that had been illuminated of the pair may turn off. However, even without having visual indicators that are illuminated, the pair of detection devices may remain engaged, meaning that a transmitter of one of the detection devices may continue to transmit a light beam to a receiver of the other detection device. For example, a receiver of a detection device may detect that a light beam has been broken. That detection device may send a message to the other detection device that includes one or more instructions that cause the other detection device (e.g., the processor of the other detection device) to cause its transmitter to continue emitting a light beam even after that light beam has been broken.

When the light beam is broken between a pair of illuminated detection devices, one or more visual indicators of one or more of the pairs may illuminate. For example, referring to FIG. 5, one or more visual indicators of the detections devices of Pair 1 500, Pair 2 502, or Pair 3 504 may illuminate. This process may repeat until an athlete stops practicing and the setting is changed.

In various embodiments, the first two detection devices that are paired together when the random pairs are set up may serve as a host pair for communications between and among one or more of the other pairs. For instance, referring to FIG. 5, detection device 506 and detection device 508 may be the first two detection devices that are paired. In this context, paired means that they are the first two detection devices whose selection mechanism is placed in a position that corresponds to the "random pairs" setting and that are arranged so the transmitter of one detection device 506 is aligned with the receiver of the other detection device 508. As such, detection devices 506, 508 may serve as a host pair.

When a light beam is broken between a pair of detection devices (referred to throughout this example as an "engaged pair"), the detection device of the engaged pair that is serving as the receiver (receiver device) may detect the breakage. The receiver device may send a message to the other detection device of the engaged pair (transmitter device). The message may include one or more instructions that cause the other detection device to cause its transmitter device to stop illuminating its visual indicators. If the engaged pair is the host pair, one or more detection devices of the host pair may randomly identify a pair of detection devices, and send a message to both detection devices of the identified pair instructing each detection device to illuminate its visual indicators.

If the engaged pair is not the host pair, the receiver device of the engaged pair may send a message to the host pair. The receiver device may send a message to either detection device of the host pair. The message may inform the host pair that light beam of the engaged pair has been broken. Upon receiving such a message from an engaged pair, one or more of the detection devices of the host pair may randomly identify a pair of detection devices, and send a message to both detection devices of the identified pair instructing each detection device to illuminate its lights. In various embodiments, the host pair may send a message to the detection device of the engaged pair that is emitting a light beam instructing that detection device to continue to emit the light beam even after the light beam has been broken.

The illumination of the visual indicators of a pair of detection devices may indicate that a game piece or a player is to break the light beam of that pair next. In "random pairs" mode, visual indicators of only one pair of detections may illuminate at a time.

As an example, referring to FIG. 5, Pair 1 500 may serve as the host pair. Pair 3 504 may currently be the engaged pair. Detection device 516 of Pair 3 504 may detect when the light beam between it and detection device 514 is broken. When it detects the breakage, detection device 516 may send a message to detection device 514 instructing detection device 514 to stop illuminating its visual indicators and/or to continue emitting the light beam. Detection device 516 may also send a message to detection device 506 and/or detection device 508 as notification that the light beam has been broken. Detection device 506 and/or detection device 508 may randomly identify a pair in the set (e.g., Pair 1, Pair 2, or Pair 3). For instance, detection device 506 and/or detection device 508 may identify Pair 2 502, and may send a message to detection device 510 and detection device 512 instructing each detection device to illuminate its visual indicators.

Figure 6:
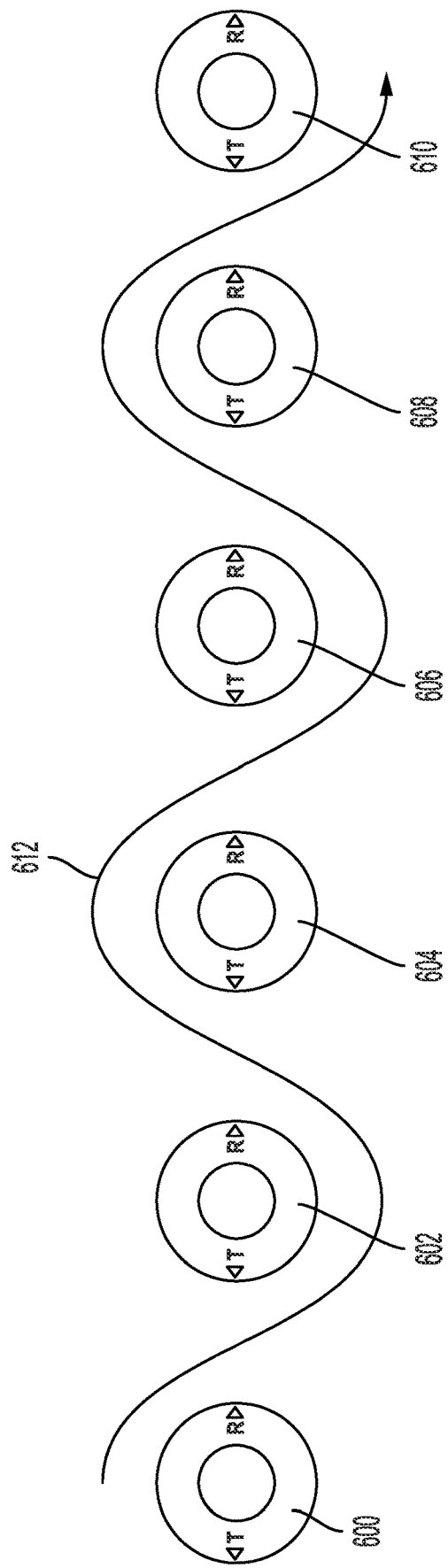
FIG. 6 illustrates an example configuration of detection devices operating in a "dribble weave (lights on)" setting.

A "dribble weave (lights on)" setting may be used to facilitate a dribble exercise or drill. Multiple detection devices may be arranged in a straight line. FIG. 6 illustrates an example configuration of detection devices operating in a "dribble weave (lights on)" setting according to an embodiment. As illustrated in FIG. 6, six detection devices (600, 602, 604, 606, 608, 610) are arranged in a straight line. FIG. 6 illustrates an example path 612 illustrating the movement of a ball (or a person) between the detection devices.

When detection devices are operating in a "dribble weave (lights on)" setting, the visual indicators of each of the detection devices having this setting may be illuminated. The visual indicators may remain illuminated until an event breaks the light beam between two adjacent detection devices. For example, referring to FIG. 6, when the light beam between detection device 600 and detection device 602 is broken, the visual indicators of detection device 600 may turn off and may remain off until the last light beam in the sequence of detection devices is broken. When the light beam between detection device 602 and detection device 604 is broken, the visual indicators of detection device 602 may turn off. This may continue until the light beam between detection device 608 and detection device 610 is broken, at which time the visual indicators of both detection device 608 and detection device 610 may turn off.

In various embodiments, the first detection device that is set to the dribble weave (lights on) setting may serve as a host device for communication between and among one or more other detection devices. For instance, referring to FIG. 6, detection device 600 may be the first detection device that is placed into a dribble weave (lights on) setting. In this context, this may mean that the detection device is the first whose selection mechanism is placed in a position that corresponds to the "dribble weave (lights on)" setting.

As other detection device are set to the dribble weave (lights on) setting, each may send a message to the host device. The message may inform the host device that the detection device is in communication. The host device may keep track of an order or sequence of connected detection devices based on the order in which messages are received from such detection devices. For example, referring to FIG. 6, host device 600 may receive a message from detection device 602, followed by detection device 604, then detection device 606, then detection device 608, then detection device 610. The host device may determine each detection device's position in line based on when its message is received.

One or more detection devices may send a message to the host detection device when a light beam it is receiving is broken. For instance, referring to FIG. 6, when the light beam between detection device 602 and detection device 604 is broken, detection device 602 may send a message to host detection device 600. The detection device that is receiving a light beam may turn off one or more of its visual indicators when it detects that the light beam it is receiving has been broken. For example, detection device 602 may cause its one or more of its visual indicators to turn off upon detecting that the light beam between it and detection device 604 has been broken.

When the host device receives a message from the last detection device in the sequence that is receiving a light beam, the host device may send a message to the last detection device in the sequence instructing it to turn off one or more of its visual indicators. For instance, referring to FIG. 6, when host device 600 receives a message from detection device 608 that the light beam between detection device 608 and detection device 610 has been broken, host device may send a message to detection device 610 instructing it to turn off one or more of its visual indicators. As explained above, the host device keeps track of the sequence of detection devices in the dribble weave (lights on) setting.

In various embodiments, the visual indicators of all of the detection devices may remain off for a period of time. For instance, once the light beam between detection device 608 and detection device 610 is broken, the visual indicators of the detection devices 600, 602, 604, 606, 608, 610 may remain off for one second. After this time period, the visual indicators of one or more of the detection devices may illuminate again to indicate that another exercise or drill can be performed. For instance, one or more detection devices of a host pair may send one or more instructions to one or more detection devices to illuminate its visual indicators.

In various embodiments, in order to place a detection device into a "dribble weave (lights on)" setting, a user may move the selection mechanism of a detection device to a position that corresponds to this setting. A user may change the setting of the detection to this setting in the order of the cones in the configuration. For example, referring to FIG. 6, detection device 600 may be changed to a "dribble weave (lights on)" setting first, followed by detection 602, detection 604, and so on. As illustrated in FIG. 6, the detection devices may be arranged so that the transmitter of one detection device is in proximity to a receiver of an adjacent detection device.

Figure 7:
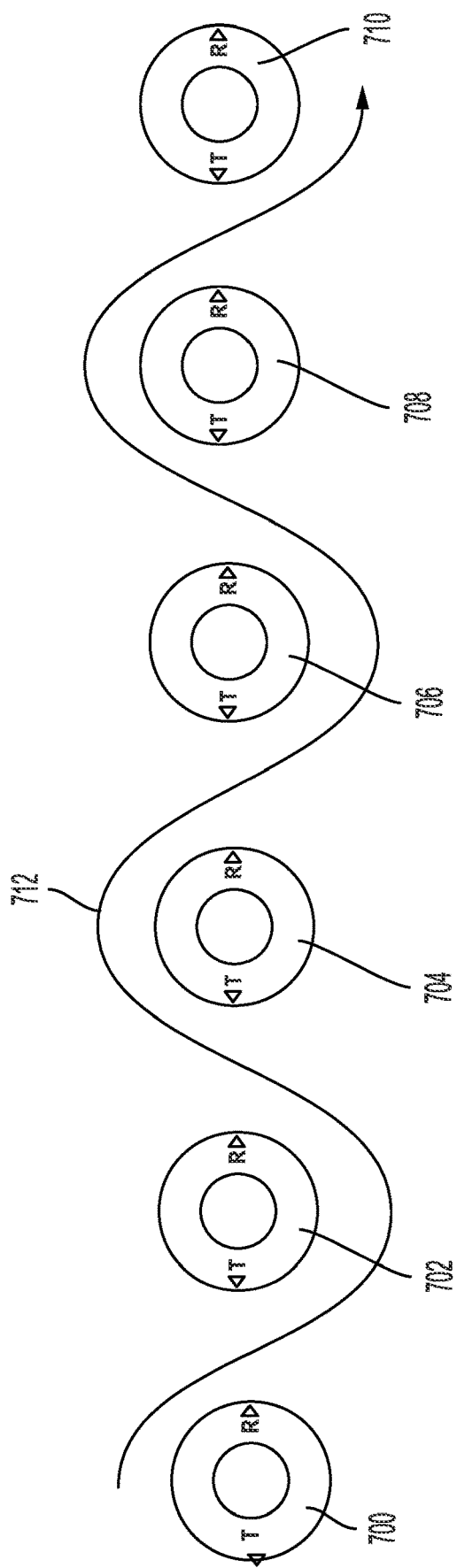
FIG. 7 illustrates an example configuration of detection devices operating in a "dribble weave (lights off)" setting.

A "dribble weave (lights off)" setting may be used to facilitate a dribble exercise or drill. Multiple detection devices may be arranged in a straight line. FIG. 7 illustrates an example configuration of detection devices operating in a "dribble weave (lights off)" setting according to an embodiment. As illustrated in FIG. 7, six detection devices (700, 702, 704, 706, 708, 710) are arranged in a straight line. FIG. 7 illustrates an example path 712 illustrating the movement of a ball (or a person) between the detection devices.

When detection devices are operating in a "dribble weave (lights off)" setting, the visual indicators of each of the detection devices having this setting may be turned off until a light beam between it and an adjacent detection device is broken. The visual indicators may remain off until an event breaks the light beam between two adjacent detection devices. For example, referring to FIG. 7, when the light beam between detection device 700 and detection device 702 is broken, the visual indicators of detection device 700 may turn on. When the light beam between detection device 702 and detection device 704 is broken, the visual indicators of detection device 702 may turn on. This may continue until the light beam between detection device 708 and detection device 710 is broken, at which time the visual indicators of both detection device 708 and detection device 710 may turn on.

In various embodiments, the first detection device that is set to the dribble weave (lights on) setting may serve as a host device for communication between and among one or more other detection devices. For instance, referring to FIG. 7, detection device 700 may be the first detection device that is placed into a dribble weave (lights off) setting. In this context, this may mean that the detection device is the first whose selection mechanism is placed in a position that corresponds to the "dribble weave (lights off)" setting.

As other detection device are set to the dribble weave (lights off) setting, each may send a message to the host device. The message may inform the host device that the detection device is in communication. The host device may keep track of an order or sequence of connected detection devices based on the order in which messages are received from such detection devices. For example, referring to FIG. 7, host device 700 may receive a message from detection device 702, followed by detection device 704, then detection device 706, then detection device 708, then detection device 710. The host device may determine each detection device's position in line based on when its message is received.

One or more detection devices may send a message to the host detection device when a light beam it is receiving is broken. For instance, referring to FIG. 7, when the light beam between detection device 702 and detection device 704 is broken, detection device 702 may send a message to host detection device 700. The detection device that is receiving a light beam may turn on one or more of its visual indicators when it detects that the light beam it is receiving has been broken. For example, detection device 702 may cause its one or more of its visual indicators to turn on upon detecting that the light beam between it and detection device 704 has been broken.

When the host device receives a message from the last detection device in the sequence that is receiving a light beam, the host device may send a message to the last detection device in the sequence instructing it to turn on one or more of its visual indicators. For instance, referring to FIG. 7, when host device 700 receives a message from detection device 708 that the light beam between detection device 708 and detection device 710 has been broken, host device may send a message to detection device 710 instructing it to turn on one or more of its visual indicators. As explained above, the host device keeps track of the sequence of detection devices in the dribble weave (lights off) setting.

The message that is sent by the last detection device in the sequence may inform the host pair that the last light beam has been broken. In various embodiments, the visual indicators of all of the detection devices may turn off for a period of time. For instance, after the light beam between detection device 708 and detection device 710 is broken, the visual indicators of the detection devices 700, 702, 704, 706, 708, 710 may remain off to indicate that another exercise or drill can be performed.

In various embodiments, in order to place a detection device into a "dribble weave (lights off)" setting, a user may move the selection mechanism of a detection device to a position that corresponds to this setting. A user may change the setting of the detection to this setting in the order of the cones in the configuration. For example, referring to FIG. 7, detection device 700 may be changed to a "dribble weave (lights off)" setting first, followed by detection 702, detection 704, and so on. As illustrated in FIG. 7, the detection devices may be arranged so that the transmitter of one detection device is in proximity to a receiver of an adjacent detection device.

In a "goal" setting, two detection devices may be placed in proximity to one another such that the transmitter of one detection device is in proximity to the receiver of the other detection device. FIG. 8 illustrates an example configuration of detection devices operating in a "goal" setting according to an embodiment.

As illustrated in FIG. 8, detection devices 800, 802 are a first pair representing a first goal, while detection devices 804, 806 are a second pair representing a second goal. When in a "goal" setting, the visual indicators of the detection devices may remain off until a light beam between a pair of detection devices is broken. For instance, referring to FIG. 8, the visual indicators of detection devices 804, 806 may remain off until the light beam between these detection devices is broken. At this time, one or more visual indicators of both detection devices 804, 806 may illuminate to indicate that a goal was made. The visual indicators may illuminate for a certain period of time (e.g., three seconds), before they may turn off.

This disclosure is not limited to the particular systems, methodologies or protocols described, as these may vary. The terminology used in this description is for the purpose of describing the particular versions or embodiments, and is not intended to limit the scope.

In this document: (i) the term "comprising" means "including, but not limited to"; the singular forms "a," "an," and "the" include plural references unless the context clearly dictates otherwise; and (iii) unless defined otherwise, all technical and scientific terms used in this document have the same meanings as commonly understood by one of ordinary skill in the art. Also, terms such as "top" and "bottom", "above" and "below", and other terms describing position are intended to have their relative meanings rather than their absolute meanings with respect to ground. For example, one structure may be "above" a second structure if the two structures are side by side and the first structure appears to cover the second structure from the point of view of a viewer (i.e., the viewer could be closer to the first structure).

The described features, structures, or characteristics may be combined in any suitable manner in one or more embodiments. In the following description, numerous specific details are provided, such as examples of agents, to provide a thorough understanding of the disclosed embodiments. One skilled in the relevant art will recognize, however, that the embodiments can be practiced without one or more of the specific details, or with other methods, components, materials, etc. In other instances, well-known structures, materials, or operations are not shown or described in detail to avoid obscuring aspects of the embodiments.

The above-disclosed features and functions, as well as alternatives, may be combined into many other different systems or applications. Various components may be implemented in hardware or software or embedded software. Various presently unforeseen or unanticipated alternatives, modifications, variations or improvements may be made by those skilled in the art, each of which is also intended to be encompassed by the disclosed embodiments.

The invention claimed is:

1. An electronic athletic training system comprising:
a first detection device comprising:
a first transmitter located on a first side of the first detection device,
a first receiver located on a second side of the first detection device, wherein the second side of the first detection device is opposite the first side of the first detection device,
one or more first visual indicators,
a first processor in communication with the first transmitter, the first receiver, and the one or more first visual indicators, and
a first computer-readable storage medium; and
a second detection device repositionable with respect to the first detection device so as to tailor a distance between the first detection device and the second detection device for a target exercise, the second detection device comprising:
a second transmitter located on a first side of the second detection device,
a second receiver located on a second side of the second detection device, wherein the second side of the second detection device is opposite the first side of the second detection device,
one or more second visual indicators,
a second processor in communication with the second transmitter, the second receiver, and the one or more second visual indicators, and
a second computer-readable storage medium;
wherein the first computer-readable storage medium comprises one or more first programming instructions that, when executed, cause the first processor to cause the first transmitter to emit a light beam to the second receiver when the first transmitter is in proximity to the second receiver;
wherein the second computer-readable storage medium comprises one or more second programming instructions that, when executed and while the second detection device is not physically coupled to the first detection device, cause the second processor to detect when the light beam is broken and perform one or more actions in response to detecting that the light beam has been broken;
wherein the first detection device further comprises a first selection mechanism having a plurality of first positions, each of the first positions corresponding to one of a plurality of first settings of the first detection device; and
wherein the plurality of first settings comprise:
an off setting;
a random pairs setting; and
at least one of:
a dribble lights on setting;
a dribble lights off setting; or
a goal setting.

2. The electronic athletic training system of claim 1, wherein the second detection device further comprises a second selection mechanism having a plurality of second positions, each of the second positions corresponding to one of a plurality of second settings of the second detection device.

3. The electronic athletic training system of claim 2, wherein the second settings comprise:
an off setting;
a random pairs setting; and
at least one of:
a dribble lights on setting;
a dribble lights off setting; or
a goal setting.

4. The electronic athletic training system of claim 1, wherein the one or more second programming instructions, when executed, cause the second processor to send a message to the first detection device, wherein the message comprises one or more instructions that instruct the first processor to:
cause one or more of the one or more first visual indicators to illuminate, or
cause one or more of the one or more first visual indicators to turn off.

5. The electronic athletic training system of claim 1, wherein the one or more second programming instructions, when executed, cause the second processor to:
cause one or more of the one or more second visual indicators to illuminate, or
cause one or more of the one or more second visual indicators to turn off.

6. The electronic athletic training system of claim 1, wherein:
the one or more second programming instructions, when executed, cause the second processor to send a message to the first detection device; and
the message comprises one or more instructions that instruct the first processor to:
cause one or more of the one or more first visual indicators to turn off; and
cause the first transmitter to continue to emit the light beam to the second receiver after the light beam has been broken.

7. The electronic athletic training system of claim 1, wherein:
the one or more second programming instructions, when executed, cause the second processor to:
cause one or more of the one or more second visual indicators to turn off, and
send a message to the first detection device; and
the message comprises one or more instructions that instruct the first processor to cause the first transmitter to continue to emit the light beam to the second receiver after the light beam has been broken.

8. The electronic athletic training system of claim 1, wherein:
the one or more first visual indicators extend along a side surface of the first detection device; and
the one or more second visual indicators extend along a side surface of the second detection device.

9. An electronic athletic training system comprising:
a first detection device comprising:
a first opening configured to receive at least a portion of a training cone,
a first transmitter located on a first side of the first detection device,
a first receiver located on a second side of the first detection device,
one or more first visual indicators,
a first processor in communication with the first transmitter, the first receiver, and the one or more first visual indicators,
a first computer-readable storage medium, and
a second detection device comprising:
a second opening configured to receive at least a portion of a training cone,
a second transmitter located on a first side of the second detection device,
a second receiver located on a second side,
one or more second visual indicators,
a second processor in communication with the second transmitter, the second receiver, and the one or more second visual indicators, and
a second computer-readable storage medium,
a third detection device comprising:
a third transmitter located on a first side of the third detection device,
a third receiver located on a second side of the third detection device, wherein the second side of the third detection device is opposite the first side of the third detection device,
one or more third visual indicators,
a third processor in communication with the third transmitter, the third receiver, and the one or more third visual indicators, and
a third computer-readable storage medium, and
a fourth detection device comprising:
a fourth transmitter located on a first side of the fourth detection device,
a fourth receiver located on a second side of the fourth detection device, wherein the second side of the fourth detection device is opposite the first side of the fourth detection device,
one or more fourth visual indicators,
a fourth processor in communication with the fourth transmitter, the fourth receiver, and the one or more fourth visual indicators, and
a fourth computer-readable storage medium,
a fifth detection device comprising:
a fifth transmitter located on a first side of the fifth detection device,
a fifth receiver located on a second side of the fifth detection device, wherein the second side of the fifth detection device is opposite the first side of the fifth detection device,
one or more fifth visual indicators,
a fifth processor in communication with the fifth transmitter, the fifth receiver, and the one or more fifth visual indicators, and
a fifth computer-readable storage medium,
a sixth detection device comprising:
a sixth transmitter located on a first side of the sixth detection device,
a sixth receiver located on a second side of the sixth detection device, wherein the second side of the sixth detection device is opposite the first side of the sixth detection device,
one or more sixth visual indicators,
a sixth processor in communication with the sixth transmitter, the sixth receiver, and the one or more sixth visual indicators, and
a sixth computer-readable storage medium,
wherein the first computer-readable storage medium comprises one or more first programming instructions that, when executed, cause the first processor to:
receive an indication that the electronic athletic training system is in a random pairs setting,
after receiving the indication, cause the one or more first visual indicators to be illuminated, and
after causing the one or more first visual indicators to be illuminated and after a first light beam between the first transmitter and the second receiver or between the first receiver and the second transmitter is broken, perform a random selection of a first pair and a second pair, the first pair being associated with the third detection device and the fourth detection device, the second pair being associated with the fifth detection device and the sixth detection device,
wherein the second computer-readable storage medium comprises one or more second programming instructions that, when executed, cause the second processor to cause the one or more second visual indicators to be illuminated when the one or more first visual indicators is illuminated;

wherein the third computer-readable storage medium comprises one or more third programming instructions that, when executed, cause the third processor to cause the one or more third visual indicators to be illuminated when the first pair is selected;

wherein the fourth computer-readable storage medium comprises one or more fourth programming instructions that, when executed, cause the fourth processor to cause the one or more fourth visual indicators to be illuminated when the first pair is selected;

wherein the fifth computer-readable storage medium comprises one or more fifth programming instructions that, when executed, cause the fifth processor to cause the one or more fifth visual indicators to be illuminated when the second pair is selected; and wherein the sixth computer-readable storage medium comprises one or more sixth programming instructions that, when executed, cause the sixth processor to cause the one or more sixth visual indicators to be illuminated when the second pair is selected.

10. The electronic athletic training system of claim 9, wherein the first detection device further comprises a first selection mechanism having a plurality of first positions, each of the first positions corresponding to one of a plurality of first settings of the first detection device.

11. The electronic athletic training system of claim 10, wherein the first settings comprise:
an off setting;
a random pairs setting; and
at least one of:
a dribble lights on setting;
a dribble lights off setting; or
a goal setting.

12. The electronic athletic training system of claim 11, wherein the second detection device further comprises a second selection mechanism having a plurality of second positions, each of the second positions corresponding to one of a plurality of second settings of the second detection device.

13. The electronic athletic training system of claim 12, wherein the second settings comprise:
an off setting;
a random pairs setting; and
at least one of:
a dribble lights on setting;
a dribble lights off setting; or
a goal setting.

14. The electronic athletic training system of claim 9, wherein:
the first programming instructions, when executed, cause the first processor to cause the one or more first visual indicators to cease being illuminated after the first light beam is broken; and the second programming instructions, when executed, cause the second processor to cause the one or more second visual indicators to cease being illuminated after the first light beam is broken.

15. The electronic athletic training system of claim 14, wherein:
the third programming instructions, when executed, cause the third processor to cause the one or more third visual indicators to cease being illuminated after a second light beam between the third transmitter and the fourth receiver or between the third receiver and the fourth transmitter is broken and the first pair is selected; and the fourth programming instructions, when executed, cause the fourth processor to cause the one or more fourth visual indicators to cease being illuminated after the second light beam is broken and the first pair is selected.

16. The electronic athletic training system of claim 15, wherein:
the fifth programming instructions, when executed, cause the fifth processor to cause the one or more fifth visual indicators to cease being illuminated after a third light beam between the fifth transmitter and the sixth receiver or between the fifth receiver and the sixth transmitter is broken and the second pair is selected; and the sixth programming instructions, when executed, cause the sixth processor to cause the one or more sixth visual indicators to cease being illuminated after the third light beam is broken and the second pair is selected.

17. The electronic athletic training system of claim 9, wherein the one or more first programming instructions that, when executed, cause the one or more first visual indicators to be illuminated while the first detection device is not physically coupled to the second detection device and is not physically coupled to the third detection device.

18. The electronic athletic training system of claim 17, wherein the one or more third programming instructions that, when executed, cause the one or more third visual indicators to be illuminated while the third detection device is not physically coupled to the first detection device and is not physically coupled to the second detection device.

19. The electronic athletic training system of claim 9, wherein:
the first opening is substantially circular;
the second opening is substantially circular;
a first underside of the first detection device comprises a first battery compartment; and
a second underside of the second detection device comprises a second battery compartment.

20. The electronic athletic training system of claim 9, wherein:
the one or more first visual indicators extend along a side surface of the first detection device; and
the one or more second visual indicators extend along a side surface of the second detection device.

* * * * *